US00PP12522P2

(12) United States Plant Patent
Olesen et al.

(10) Patent No.: US PP12,522 P2
(45) Date of Patent: Apr. 9, 2002

(54) FLORIBUNDA ROSE PLANT NAMED 'POULJILL'

(76) Inventors: L. Pernille Olesen; Mogens N. Olesen, both of Hillerødvejen 49, DK-3480 Fredensborg (DK)

( * ) Notice: Subject to any disclaimer, the term of this patent is extended or adjusted under 35 U.S.C. 154(b) by 0 days.

(21) Appl. No.: 09/261,446

(22) Filed: Mar. 3, 1999

(51) Int. Cl.[7] ..... A01H 5/00
(52) U.S. Cl. ..... Plt./145
(58) Field of Search ..... Plt./145, 143, 141

(56) References Cited

PUBLICATIONS

Certificate of Grant of Plant Breeders Rights—DK PBR 16587, dated Jul. 6, 1994.*

Certificate of Grant of Plant Breeders Rights in Poland, dated Feb. 22, 1999 PL PBR O00860.*

Application for Community Plant Variety—European Union #0588/95, dated Aug. 8, 1995 with proposal for variety denomination—EU 2035.*

UPOV–ROM , 2000/04, Plant Variety Database, GTI JOUVE Retrieval Software, 3 citations for 'POULjill'.*

* cited by examiner

*Primary Examiner*—Howard J. Locker

(57) ABSTRACT

A new garden rose plant which has abundant, yellow flowers and attractive foliage. This new and distinct variety has shown to be uniform and stable in the resulting generations from asexual propagation.

2 Drawing Sheets

SUMMARY OF THE INVENTION

The present invention constitutes a new and distinct variety of garden rose plant which originated from a controlled crossing between unnamed seedling and 'Avignon'. The two parents were crossed and the resulting seeds were planted in a controlled environment. The new variety is named 'POULjill'.

The new rose may be distinguished from its seed parent, an unnamed seedling, by the following combination of characteristics:

1. The seed parent is a smaller plant with bushy, compact growth.
2. The seed parent has smaller flowers when compared to 'POULjill'.

The new variety may be distinguished from its pollen parent, 'Avignon' created by the same inventors, by the following combination of characteristics:

1. The pollen parent flower has 23 petals; whereas 'POULjill' has 35–40 petals.
2. The pollen parent flower is smaller, when the flower is fully open is typically 50 mm in diameter; whereas 'POULjill' is 70–85 mm in diameter.
3. 'POULjill' exhibits a stronger fragrance than the pollen parent. The pollen parent's fragrance can be described as slight, whereas 'POULjill's' fragrance can be described as moderate.

The objective of the hybridization of this rose variety for garden use was to create a new and distinct variety with unique qualities, such as:

1. Uniform and abundant flowers;
2. Vigorous, compact growth;
3. Disease resistance.
4. Fragrance.

This combination of qualities is not present in previously available commercial cultivars of this type and distinguishes 'POULjill' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULjill' was selected in Spring 1990 by the inventors as a single plant from the progeny of the aforementioned hybridization.

Asexual reproduction of 'POULjill' by traditional budding was first done by L. Pernille and Mogens N. Olesen in August, 1990 in Fredensborg, Denmark. This initial and other subsequent propagations were conducted in controlled environments have demonstrated that the characteristics of 'POULjill' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULjill'. Specifically illustrated in SHEET 1:

1. Stem showing branching and the attachment of leaves, buds, and peduncles;

2. Flower bud, partially opened bud, and open bloom;

3. Flower petals, detached;

4. Sepals and pedicel;

5. Flowering stem as well as a bare stem exhibiting thorns;

6. Leaves.

DETAILED DESCRIPTION OF THE VARIETY

The following is a description of 'POULjill', as observed in its outdoor growth in a field nursery in Jackson County, Oreg. Observations were conducted during October, 1998. Color references are made using The Royal Horticultural Society (London, England) Colour Chart, 1995, except where common terms of color are used.

For a comparison, several physical characteristics of the rose variety 'POULjill', a grandiflora rose variety from the same inventors described and illustrated in U.S. Plant Pat. No. 8,230 and issued on May 18, 1993 and is compared to 'POULjill' in Chart 1.

CHART 1

| | 'POULjill' | 'POULbero' |
|---|---|---|
| Number of flower petals | Double 35–40 petals. | Double 20–23 petals. |
| Color of Blooms | Warm yellow. | Blend of red, orange, yellow and pink tones. |
| Plant Size | 100 cm (h) × 100 cm (w). | 100 cm (h) × 120 cm (w). |

Parents:
*Seed parent.*—Unnamed seedling.
*Pollen parent.*—'Avignon'.
Classification:
*Botanical.*—*Rosa hybrida.*
*Commercial.*—Floribunda.

FLOWER AND FLOWER BUD

Blooming habit: Recurrent.
Flower bud:
*Size.*—Upon opening, 35 mm in length from base of receptacle to end of bud.
*Bud form.*—Short and pointed ovoid.
*Bud color.*—As sepals unfold, Yellow Group 2D with slight variegations of Red Group 51A–51B. Yellow-Orange Group 18B at ¼ opening.
*Sepals.*—Green Group 144A. Moderate foliaceous appendages on three of the five sepals. Interior surfaces of sepals are moderately pubescent with limited pubescence on the exterior of sepal. A limited number of stipitate glands are located on margins of sepals.
*Receptacle.*—Surface: Generally smooth, very few stipitate glands noted. Shape: Funnel shaped. Size: Medium. 8 mm (h)×6 mm (w). Color: Yellow-Green Group 144B with some anthocyanin noted in color range of Greyed-Purple Group 185D.
*Peduncle.*—Surface: There are a significant number of stipitate glands and prickles in comparison to the smooth receptacle. Length: 30–65 mm average length. Color: Yellow-Green Group 144C. Anthocyanin color of Greyed-Purple Group 184D. Strength: Upright.
*Borne.*—Multiple buds per stem in the range of 2 to 10 buds. Generally, in the range of 4 to 8 buds per flowering stem.
Flower bloom:
*Fragrance.*—Moderately strong fruit-like scent.
*Duration.*—As a cut flower 4 to 5 days. The blooms have a duration on the plant of approximately 6 to 7 days. Petals fall cleanly away from plant.
*Size.*—Average flower diameter is 70–85 mm when open.
*Form.*—Shape of flower when viewed from the side: Upon opening, upper part: Flat. Upon opening, lower part: Flat. Open flower, upper part: Flattened convex. Open flower, lower part: Concave.
*Petalage.*—Double. Average range: 35–40 petals under normal conditions with 0–5 petaloids.
Color:
*Upon opening, petals.*—Outermost petals: Upper Surface: Yellow Group 13B with marginal zone Yellow Group 11D. Reverse Side: Yellow Group 13B with variegation of Red Group 51A–54B. Innermost petals: Upper Surface: Yellow Group 9B–9C. Reverse Side: Yellow Group 12C with variegation in marginal zone in Red Group 37B.
*Upon opening, basal petal spots.*—Outermost petals: Upper Surface: Yellow Group 12A. Reverse Side: Yellow Group 12A. Innermost petals: Upper Surface: Yellow Group 13B. Reverse Side: Yellow Group 9A.
*After opening, petals.*—Outermost petals: Upper Surface: Yellow Group 4C. Reverse Side: Yellow Group 4D. Innermost petals: Upper Surface: Yellow Group 8C with marginal variegation in Red Group 37C. Reverse Side: Yellow Group 8B.
*After opening, basal petal spots.*—Outermost petals: Upper Surface: Yellow Group 7A. Reverse Side: Yellow Group 7B. Innermost petals: Upper Surface: Yellow Group 7A. Reverse Side: Yellow Group 7A.
General tonality: On open flower Yellow Group 12B–12C. No change in the general tonality at the end of the 2nd day. Afterwards, general tonality is Yellow Group 12C–12D.
Petals:
*Petal reflex.*—Slightly reflexed.
*Petal edge.*—Is notched in center of margin.
*Shape.*—Deltoid shaped.
*Petaloids.*—Present. Quantity: 0–5.
*Thickness.*—Thin petal texture.
*Arrangement.*—Informal.
Reproductive organs:
*Pollen.*—Color: Yellow-Orange Group 21A. Abundance: Average.
*Anthers.*—Size: Medium. Color: Yellow Group 3C. Abundance: Average.
*Filaments.*—Color: Yellow Group 14B.
*Stigmas.*—Slightly superior in location to anthers. Color: Green-Yellow Group 1C.
*Styles.*—Color: Green-Yellow Group 1C. Other intonation: Red Group 51C located on styles just below the stigma.
*Hips.*—None observed.

PLANT

Plant growth: Bushy. When grown as a budded field grown plant on *Rosa multiflora* understock, the average height of the plant itself is 100 cm and the average width is 100 cm.
Stems:
*Color.*—Young wood: Yellow-Green Group 144B. Older wood: Yellow-Green Group 144C.

*Thorns*.—Incidence: Few almost thornless. Size: Average length: 6 mm. Color: Greyed-Orange Group 166D. Shape: Concave.

*Surface*.—Young wood: Smooth. Older wood: Smooth.

Plant foliage: Normal number of leaflets on normal leaves in middle of the stem: 5 leaflets.

*Leaf size*.—Medium. 100 mm (l)×75 mm (w).

*Abundance*.—Above average quantity of foliage.

*Color*.—Upper Leaf Surface: Green Group 137A. Lower Leaf Surface: Green Group 137D. Juvenile foliage: Upper Surface, Green Group 143B, with intonations of Greyed-Purple Group 184D. Lower Surface Green Group 137B. Anthocyanin intonation: Yes. Location: Leaf margins. Color: Greyed-Purple Group 184D.

Plant leaves and leaflets:

*Stipules*.—Size: 20 mm. Color: Yellow-Green Group 144C. Stipitate glands: Moderate number located along the margin.

*Petiole*.—Length: 30 mm–35 mm. Color: Yellow-Green Group 144A. Underside: Smooth. Margins: Stipitate glands in moderate numbers.

*Rachis*.—Color: Yellow-Green Group 144A. Underside: Very small light Yellow prickles. Margins: Very few Stipitate glands.

Leaflet:

*Edge*.—Finely serrated.

*Shape*.—Ovate. Terminal leaflet more pointed than other leaflets.

*Other*.—Thick, matte leaves on Mature foliage.

Disease resistance: Above average resistance to mildew, rust, black spot, and Botrytis under normal growing conditions in Jackson County, Oreg. Presence of powdery mildew is limited to peduncle and receptacle in un-sprayed field with large amount of inoculant present.

Cold hardiness: The variety 'POULjill' has been found to be cold hardy in Fredensborg, Denmark and Jackson County, Oreg.

We claim:

1. A new and distinct variety of rose plant of the Floribunda class, substantially as herein illustrated and described as a distinct and novel rose variety due to its abundant flowers, vigorous growth, disease resistance, and extended period of bloom.

* * * * *

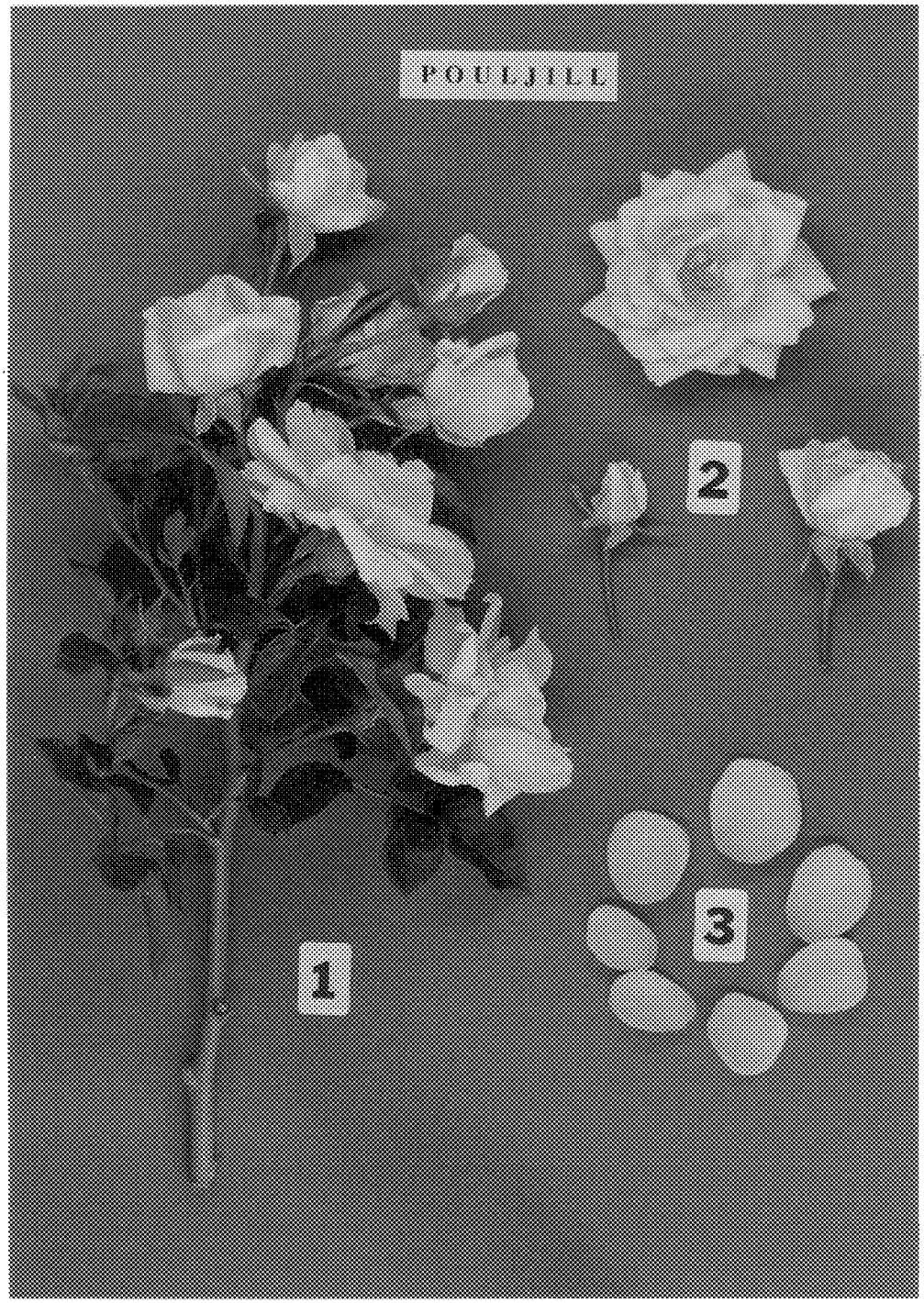
POULJILL
1
2
3

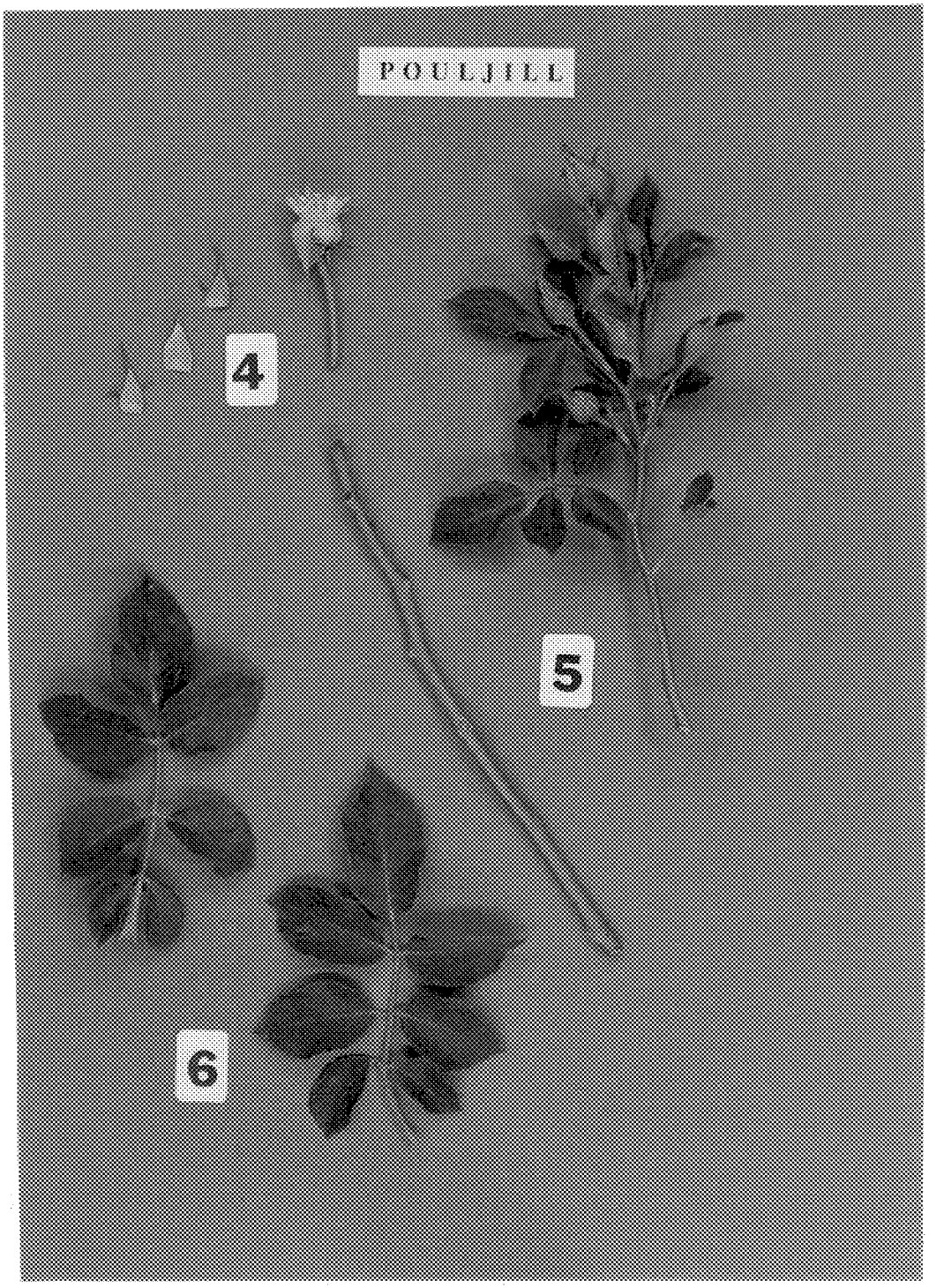
POULJILL
4
5
6